(12) United States Patent
Berube et al.

(10) Patent No.: US 6,463,791 B1
(45) Date of Patent: Oct. 15, 2002

(54) WELD TESTING ASSEMBLY

(76) Inventors: Guy Berube, 880 Guthrie, Sarnia, Ontario (CA), N7V 1Y3; Glenn Carson, 1362 Catheart Boulevard, Sarnia, Ontario (CA), N7S 5G5

( * ) Notice: Subject to any disclaimer, the term of this patent is extended or adjusted under 35 U.S.C. 154(b) by 11 days.

(21) Appl. No.: 09/705,856

(22) Filed: Nov. 3, 2000

Related U.S. Application Data

(63) Continuation-in-part of application No. 09/277,493, filed on Mar. 26, 1999, now abandoned, which is a continuation-in-part of application No. 08/973,168, filed on Feb. 13, 1998, now abandoned.

(51) Int. Cl.[7] ............... G01M 3/04; G01M 3/28; G01N 3/12; B23K 31/02
(52) U.S. Cl. ............................. 73/49.8; 73/46
(58) Field of Search ...................... 73/46, 49.8

(56) References Cited

FOREIGN PATENT DOCUMENTS

| JP | 55-94131 | 7/1980 | ............ 73/46 |
|---|---|---|---|
| JP | 57-190243 | 11/1982 | ............ 73/46 |
| JP | 61-59239 | 3/1986 | ............ 73/46 |
| JP | 62-174624 | 1/1988 | ............ 73/46 |

Primary Examiner—Daniel S. Larkin
(74) Attorney, Agent, or Firm—Ladas & Parry

(57) ABSTRACT

The invention provides an assembly for hydrostatic testing of welds between components, such as but not limited to welds which connect components such as nozzles (2) or patches (40) to a pressure vessel (1). A sealing body (8) is secured against one of the components to define a sealed space (25) adjacent to the weld (5) to be tested. The body is secured by at least one tie rod (9), positioned to pull the body against the component by tightening of a nut (12). Pressure testing can then be carried out by introducing pressurized fluid into the sealed space and applying appropriate monitoring techniques to check for leakage.

6 Claims, 17 Drawing Sheets

WELD TESTING ASSEMBLY

This application is a continuation-in-part of U.S. application Ser. No. 09/277,493, filed Mar. 26, 1999, now abandoned, which is a continuation-in-part of U.S. application Ser. No. 08/973,168, filed Feb. 13, 1998 (now abandoned).

BACKGROUND OF THE INVENTION

This invention relates to the testing of welds, and particularly but not necessarily, the hydrostatic testing of welds for nozzles, studs, flanges, patches, etc. on or connected to pressure tanks or vessels.

The testing of weld integrity on nozzles or other components welded to pressure vessels traditionally involves the whole vessel having to be filled with a pressurizing fluid medium. This usually means that a large volume of fluid is required, and, if the fluid is not used in the actual operation of the system of which the vessel is a part, purging of the equipment has to be performed both before and after weld testing.

SUMMARY OF THE INVENTION

In one embodiment, the present invention provides a weld testing assembly for hydrostatic pressure testing of welds between two components, the weld testing assembly comprising:

a body securable against at least one surface of at least one of the components so as to define a sealed space adjacent to the weld to be tested; and, at least one port for receiving a pressurized test fluid into the sealed space;

the body being provided with one or more threaded tie rods and one or more nuts adapted to be threaded on the tie rods;

wherein the weld is provided between a vessel and a patch thereon, and wherein the at least one tie rod is secured to the patch and tightening of the nut forces the body against the patch, the body extending beyond the patch such that the sealed space includes the weld.

In another embodiment, the invention provides a method for testing a weld between a first component and a patch on the first component, comprising the steps of:

providing a sealing assembly comprising a body adapted to be forced into engagement with at least one surface of the first component, the body extending beyond the patch;

providing at least one threaded tie rod secured to the patch;

securing the sealing assembly against the at least one surface so as to define a sealed space adjacent to, and including, the weld to be tested, the sealing assembly being secured against the at least on surface by tightening a nut on each of the at least one threaded tie rod such that tightening of the nut pulls the body towards the patch;

injecting a pressurized test fluid into the sealed space; and monitoring the sealed space for indicia of a leak of the test fluid from the sealed space.

In a further embodiment, the invention provides a weld testing assembly for hydrostatic pressure testing of welds between two components, the weld testing assembly comprising:

a body securable against at least one surface of at least one of the components so as to define a sealed space adjacent to the weld to be tested; and, at least one port for receiving a pressurized test fluid into the sealed space;

the body being provided with one or more threaded tie rods and one or more nuts adapted to be threaded on the tie rods;

wherein the body is comprised of two or more sections, each of the sections including a means for joining the sections together to form the body.

Further features of the invention will be described or will become apparent in the following description.

BRIEF DESCRIPTION OF DRAWINGS

In order that the invention may be more clearly understood, the preferred embodiment thereof will now be described in detail by way of example, with reference to the accompanying drawings, in which.

DETAILED DESCRIPTION OF THE PREFERRED EMBODIMENTS

Figure 1:
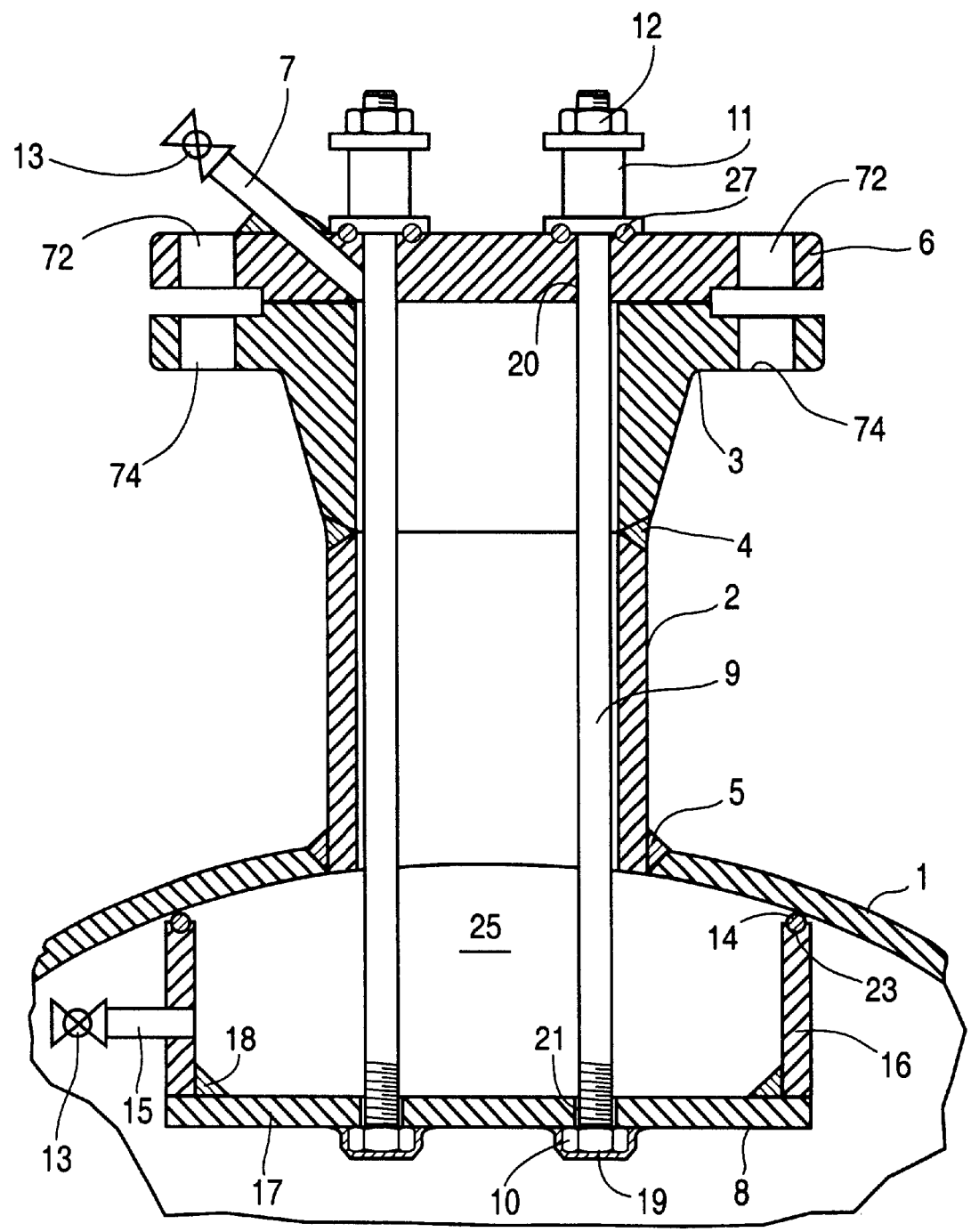
FIG. 1 is a cross-sectional view of one embodiment of a weld testing assembly for a nozzle extending from a pressure vessel.

FIG. 1 shows a weld testing assembly configured to test a weld 5 which holds a nozzle 2 in a hole in the wall of a pressure vessel 1. A flange 3 is mounted on the nozzle 2 via a flange weld 4. The weld testing assembly is secured against the inner wall of the vessel, to define a sealed area 25. The assembly has an external blind 6, which matches the form and shape of the flange 3. The blind can be mounted on the flange using any appropriate fastening means, such as nuts and bolts, through corresponding holes in the flange and the blind. There is at least one hole 20 in the blind 6, and normally several such holes, each such holes accommodating a threaded tie rod 9. The tie rod 9 connects the blind 6 to a body 8, which is situated inside the pressure vessel 1 and which has walls 16 which seal against the wall of the pressure vessel, outside the nozzle weld 5. The seal is achieved by any suitable means, such as by using a rubber O-ring 14, held in place by a groove 23 at the end of the walls 16. A lead seal could be used as one alternative. Each tie rod 9 passes through a hole 21 in the body and is threaded into a nut 10. Each nut 10 is sealed to the body by a seal weld 19.

The tie rods 9 pull the body 8 towards the blind 6, via tightening of the nuts 12, to create the sealed area 25. Preferably, a packing box 11 is used to provide an effective seal where the tie rods extend through the blind, the packing box being mounted on the tie rod 9 on the outside of the blind 6. In the preferred embodiments, an O-ring 27, preferably accommodated in suitable grooves in the packing box and the blind, provides a seal between the packing box assembly and the blind. When the nut 12 is tightened, it creates a seal to define the sealed area 25, but it also produces a longitudinally-oriented mechanical stress in the nozzle weld 5. Accordingly, the weld's ability to withstand the mechanical stress in addition to the hydrostatic pressure created by the pressurizing fluid during the test provides the operator with additional confidence in the integrity of the weld, because it will have to withstand more stress than it will experience during normal operational use.

Clearly, alternative tightening and sealing arrangements could be used, and the use of such alternatives is within the scope of this invention.

In the embodiment shown in FIG. 1, the body 8 is generally cup-shaped, having a disc 17 to which the wall 16 is via a body weld 18. The disc has one hole 21 for each tie rod 9.

The weld testing assembly also has vent and filler pipes 7 and 15 respectively, each communicating with the sealed area 25, for passage of pressure testing fluid into and from the sealed area. The pressurizing fluid is normally water, or conventional antifreeze if the test is carried out in cold temperatures. However, it should be understood that any number of different fluids, such as atmospheric air, nitrogen, or an inert gas, may also be used. Ports to accommodate a vent and filler pipe can be situated in the blind 6 (vent and filler port 7) or in the body 8 (vent and filler port 15) or in both (as illustrated in FIG. 1). The vent and filler pipe are connected to a pressurized fluid media container and a purge fluid container via one or more valves 13, shown schematically in FIG. 1. If desired, a single port can be used for both filling and venting, although purging of the test fluid may then be less effective.

With the invention, pressurizing the sealed area 25 with fluid can thus readily be achieved, in order to test the strength and integrity of the weld using conventional monitoring means, e.g. visual leak inspection, measurement of pressure drop, measurement of flow, etc. Of course, for a secure weld, there should be no pressure drop or fluid flow once the sealed area is pressurized.

Figure 2:
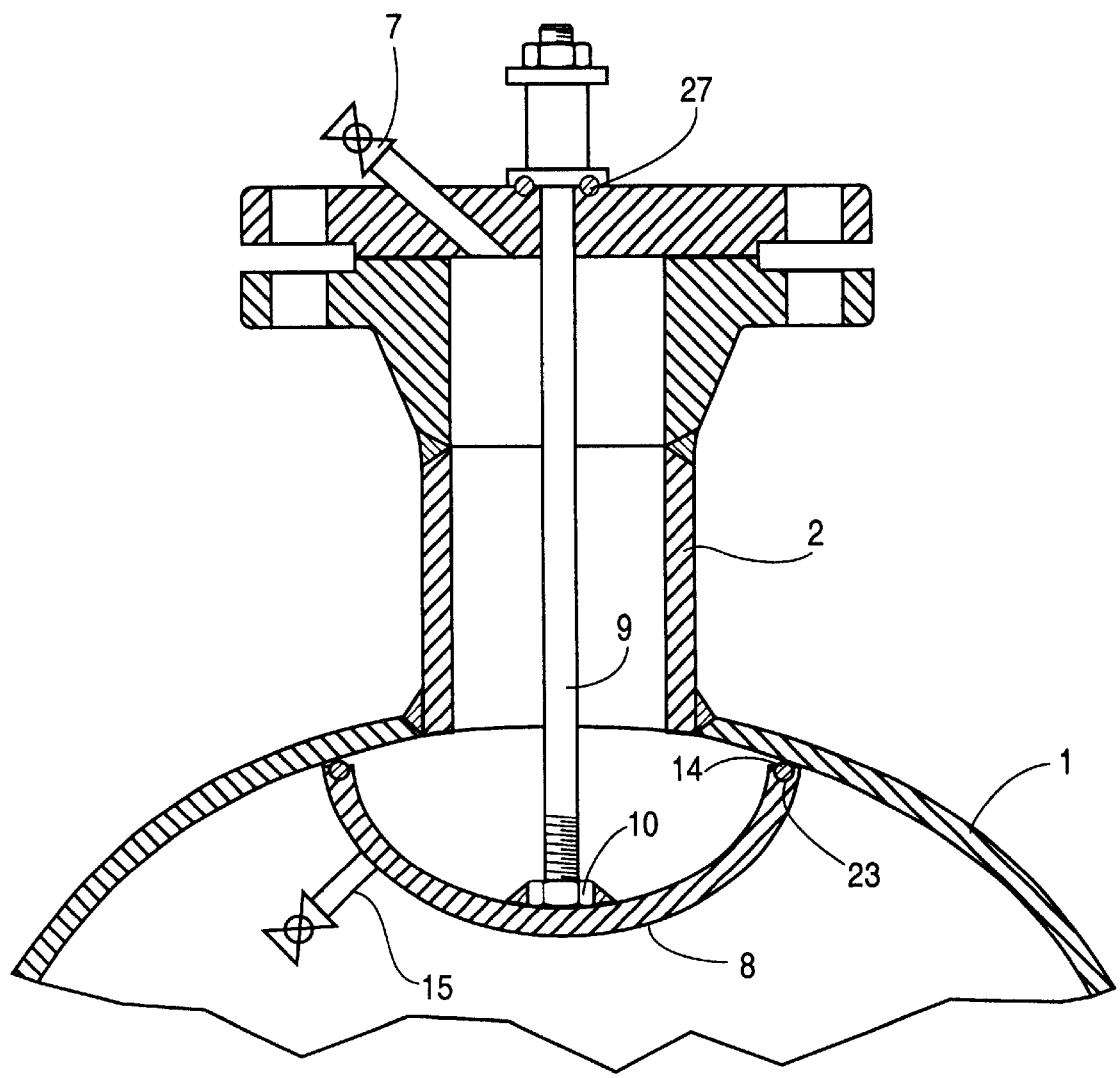
FIG. 2 is a cross-sectional view of an alternative weld testing assembly for a nozzle.

FIG. 2 shows an alternative embodiment for the weld testing assembly, where the body 8 is a one-piece hemispherical shape. A groove 23 is defined within the edge of the body to accommodate a seal 14, as in the embodiment of FIG. 1.

Figure 3:
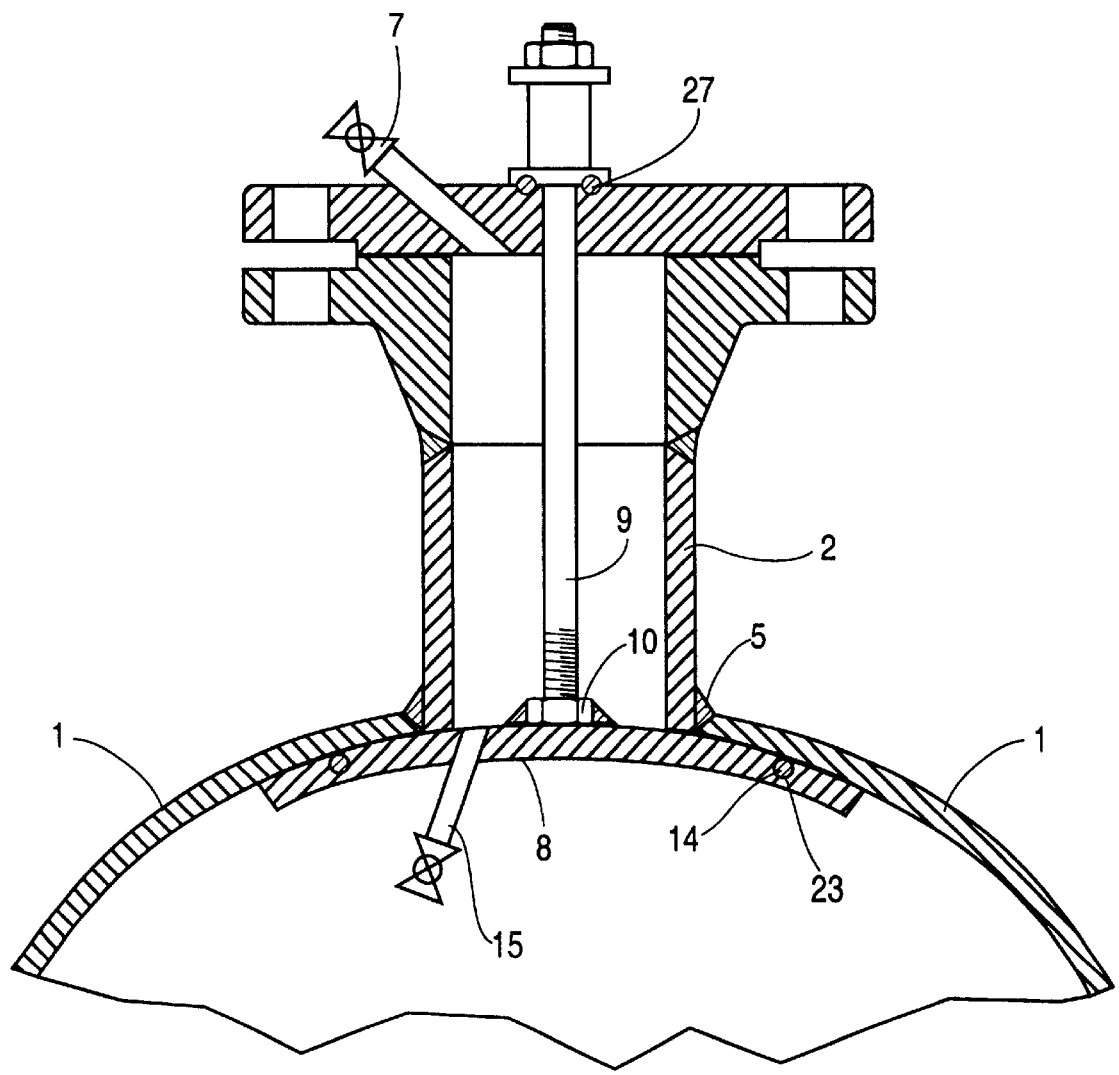
FIG. 3 is a cross-sectional view of another alternative weld testing assembly for a nozzle.

FIG. 3 shows another alternative embodiment of the weld testing assembly, where the body 8 is one piece which conforms to the shape of the inside of the vessel 1, in the area adjacent the weld. There is a groove 23 in the body, to hold the seal 14.

Figure 4:
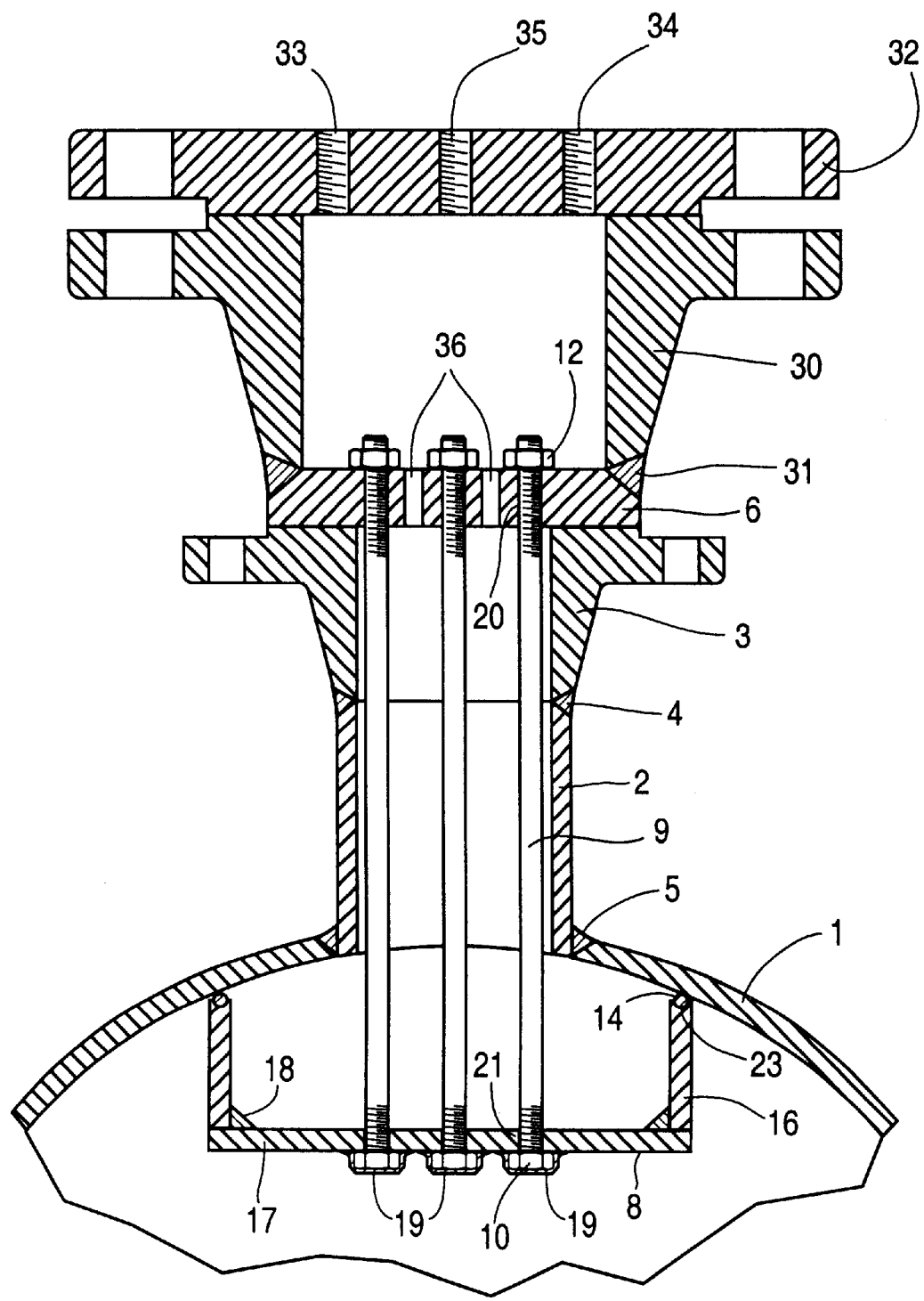
FIG. 4 is a cross-sectional view of a more complex weld testing assembly for a nozzle, useful for large welds.

FIG. 4 shows another alternative embodiment of the weld testing assembly configured to test a weld attaching a nozzle to a pressure vessel. This embodiment is particularly advantageous for a pressure test where the circumference of the weld to be tested is so large that three or more tie rods 9 are required to maintain the seal. This configuration provides a cost and time savings by eliminating the requirement of sealing every tie rod using a packing box. Instead, the threaded tie rods are tightening against the external blind 6 by conventional nuts to create a seal between the pressure vessel and the body 8 and between the circumferential edges of the flange 3 and the external blind. A conventional wellneck flange 30 is secured to the top of the external blind by a weld 31. A second external blind 32 is sealably connected to the wellneck flange using conventional studs (not shown) to seal the top of the test assembly. Three threaded openings are drilled in the second external blind to provide a vent port 33, a filler port 34, and a gauge port 35. During the pressure test, fluid is introduced through the filler port 34, and a gauge port 35. During the pressure test, fluid is introduced through the filler port and passes through holes 36 drilled in the external blind 6.

Figure 5:
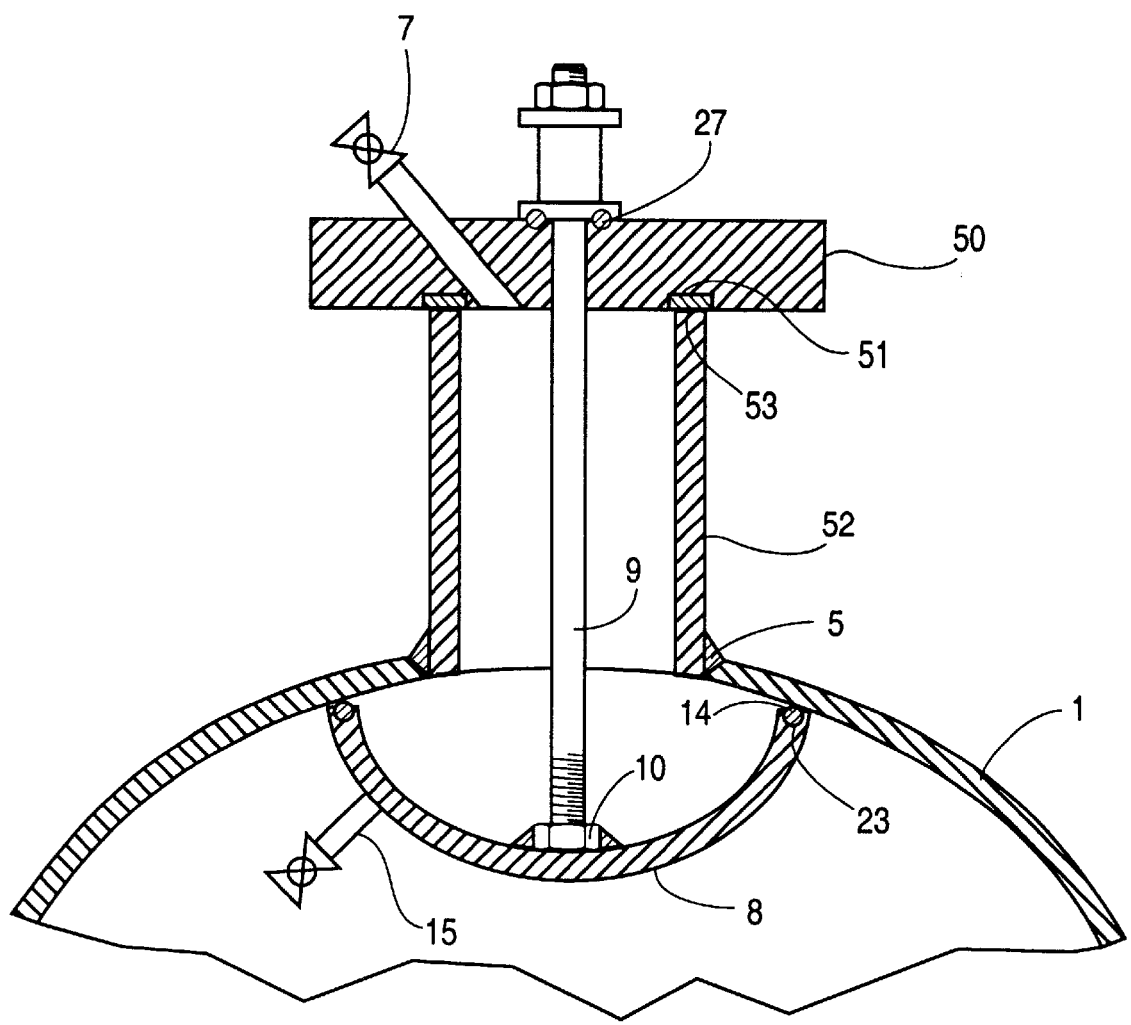
FIG. 5 is a cross-sectional view of a weld testing assembly for a spigot extending from a pressure vessel.

FIG. 5 shows an alternative embodiment of the weld testing assembly configured to test a weld 5 securing a spigot 52 to the wall of a pressure vessel. A groove 51 is machined in a cylindrical plate 50, such that the spigot fits tightly into the groove. To create a seal between the plate and the spigot, an O-ring 53 is inserted into the groove and then the plate is fitted onto the spigot. The assembly is then tightened using the rod, packing box, and nuts, as previously described.

Figure 6:
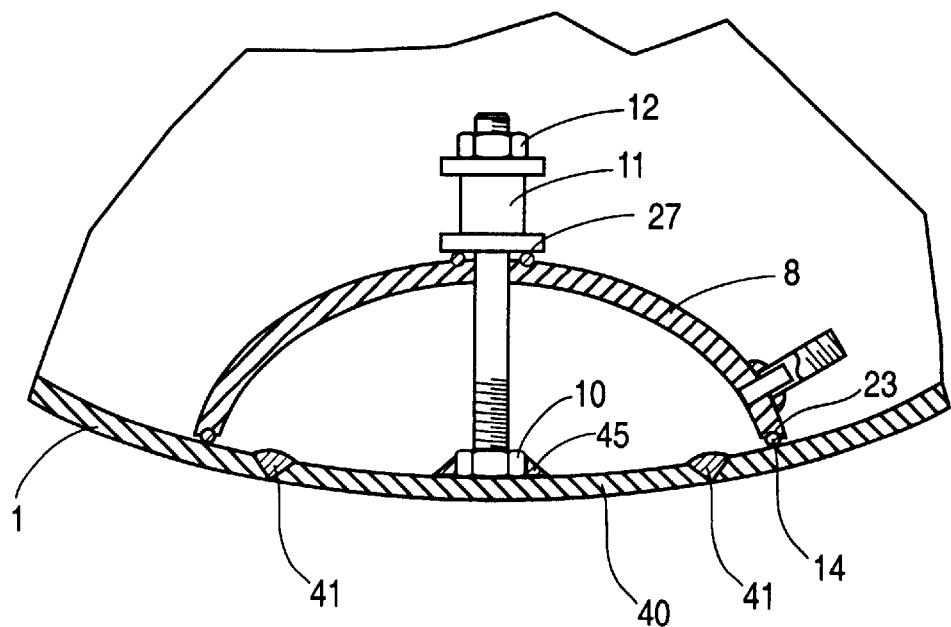
FIG. 6 is a cross-sectional view of a weld testing assembly for a patch in the wall of a pressure vessel.

FIG. 6 shows an alternative embodiment of the weld testing assembly configured to test a weld 41 securing a patch 40 to the wall of a pressure vessel. A tie rod seals the body against the inside of the pressure vessel. The body has a sealing circumference around the patch and the seal between the body and the pressure vessel is accomplished by an O-ring 14 which fits into a groove 23 in the body, as described above. To provide a second seal between the body and the opening to accommodate the tie rod, preferably a packing box 11 and a second O-ring 27 are provided. The tie rod is screwed into the first nut 10, which is welded onto the patch by an ordinary fillet weld 45. The assembly is sealed by tightening the second nut 12, as described previously.

In certain situations, it may be advantageous to pre-weld the first nut 10 to the patch in anticipation of conducting the hydrostatic test using the invention.

Figure 7:
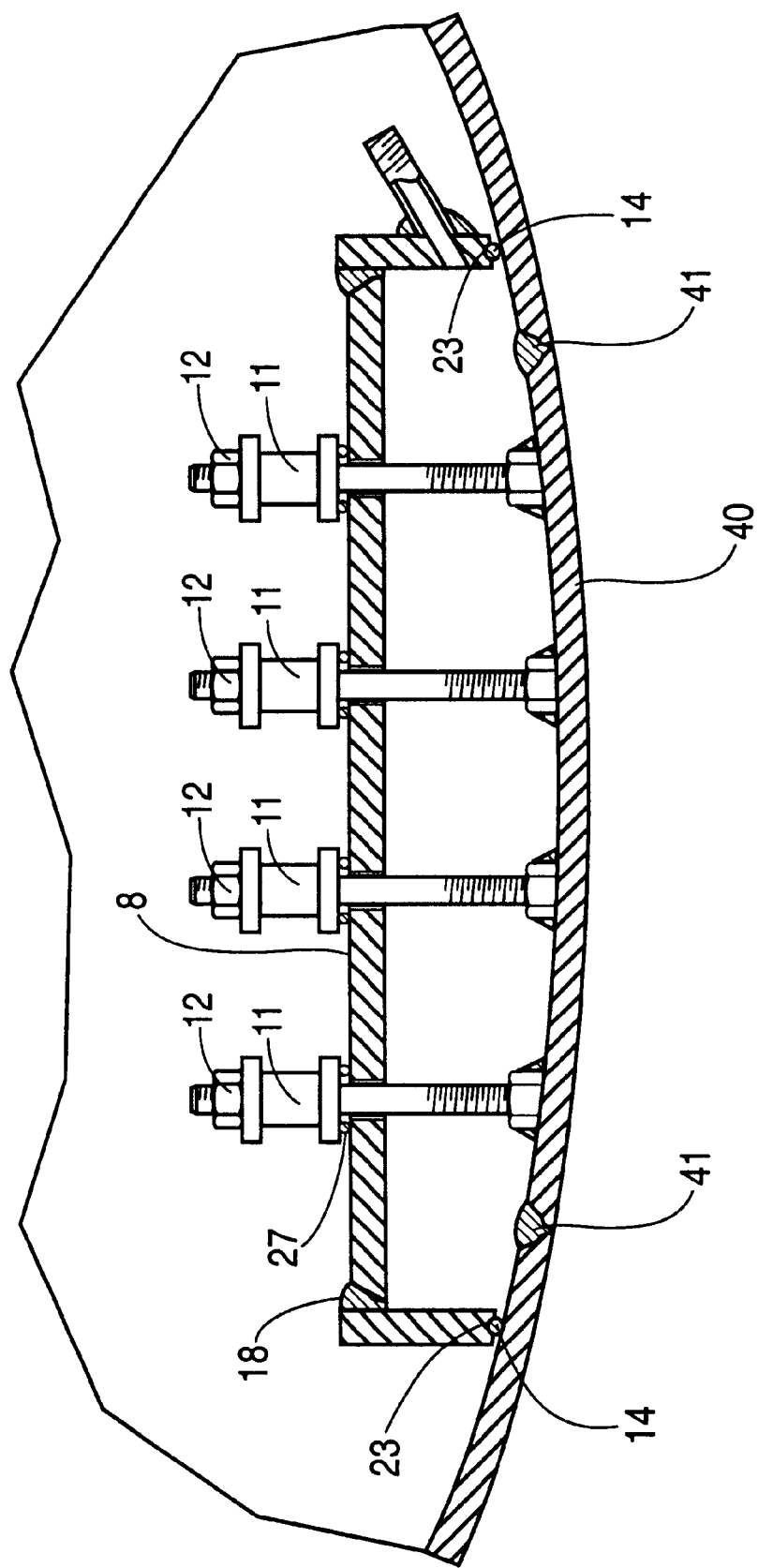
FIG. 7 is a cross-sectional view of an alternative embodiment of a weld testing assembly for a patch.

FIG. 7 shows an alternative embodiment of the weld testing assembly configured to test a weld securing a patch to the wall of a pressure vessel. This embodiment is required when the patch is so large that the circumference of the weld to be tested requires more than one tie rod to maintain the seal during the pressure test.

Figure 8:
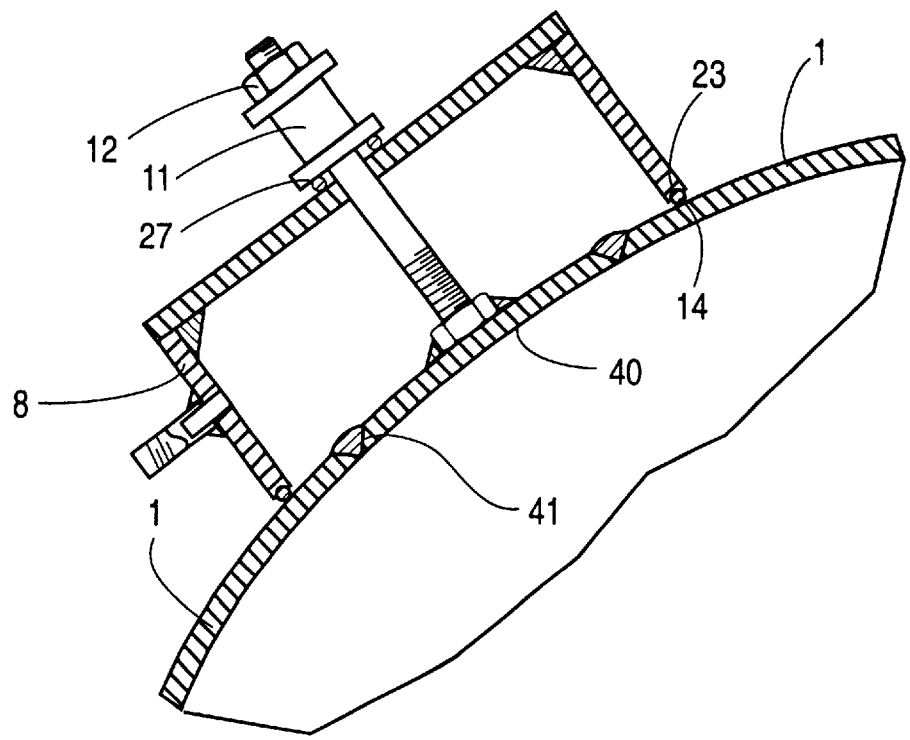
FIG. 8 is a cross-sectional view of another alternative embodiment of a weld testing assembly for a patch.

FIG. 8 shows an alternative embodiment of the weld testing assembly configured to test a weld securing a patch to the wall of a pressure vessel, where the assembly is sealed against the outside of the vessel.

It will be understood that the materials for the components of the weld test assembly have to be chosen according to the specific demands of the particular pressure vessel environment to be tested. In most cases, a carbon steel body will suffice. In other cases, a stainless steel body will have to be employed.

It should be appreciated that although the invention is particularly adapted to use in testing welds in pressure vessels, as described above, the invention can be readily adapted to testing any other welds, whether in pressure vessels or elsewhere.

The invention provides an effective and efficient means for testing the integrity of welds, particularly but not necessarily only in pressure vessels.

Returning to FIG. 1, as mentioned previously, the external blind 6 is preferably mounted to the flange 3 by means of bolts, which extend through the holes 72 and 74 in the blind 6 and flange 3, respectively. This arrangement ensures that the blind 6 is properly positioned over the flange 3 so that the required seal is established. Further, in such arrangement, the tie rods 9 only serve to draw the body 8 towards the blind 6 to create the required seal for conducting the test.

Figure 9:
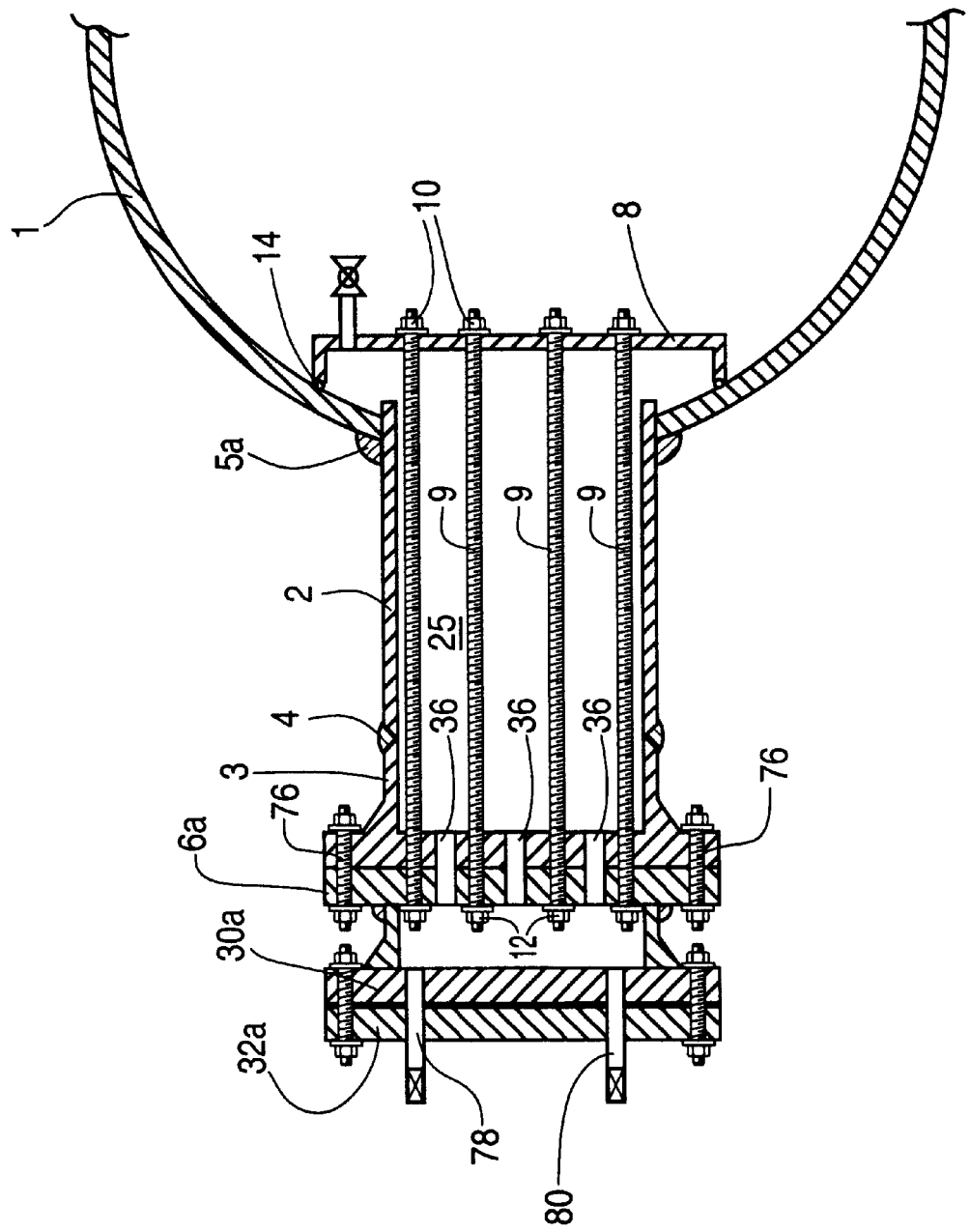
FIGS. 9 to 15 show cross-sectional views of alternate embodiments of the invention.

FIG. 9 illustrates a further embodiment of the invention similar to that of FIG. 4 with different but similar elements being designated with the letter "a" for convenience. As shown, the weld testing assembly includes a body 8, which may be of a single piece or a combination of pieces as described above. The body 8 is placed inside of a pressure vessel 1 and includes an O-ring 14 to effect sealing of the body 8 against it. Tie rods 9 extend from the body 8 to the external blind 6a is mounted to the flange 3 by means of bolts 76, which secure the blind 6a to the flange 3. As mentioned above, such arrangement ensures that the blind 6a is properly placed and secured against the flange 3. As before, the blind 6a and the flange 3 are provided with openings 36 to enable the pressurized fluid for the test to enter the sealed area 25. A wellneck flange 30a is attached to the blind 6a by welding. A second external blind 32a is then bolted on the wellneck flange 30a. Both the wellneck flange 30a and the second blind 32a are provided with openings through which extends ports 78 and 80 for filling and venting the sealed area 25 and, if required, for providing a pressure gauge.

Figure 10:
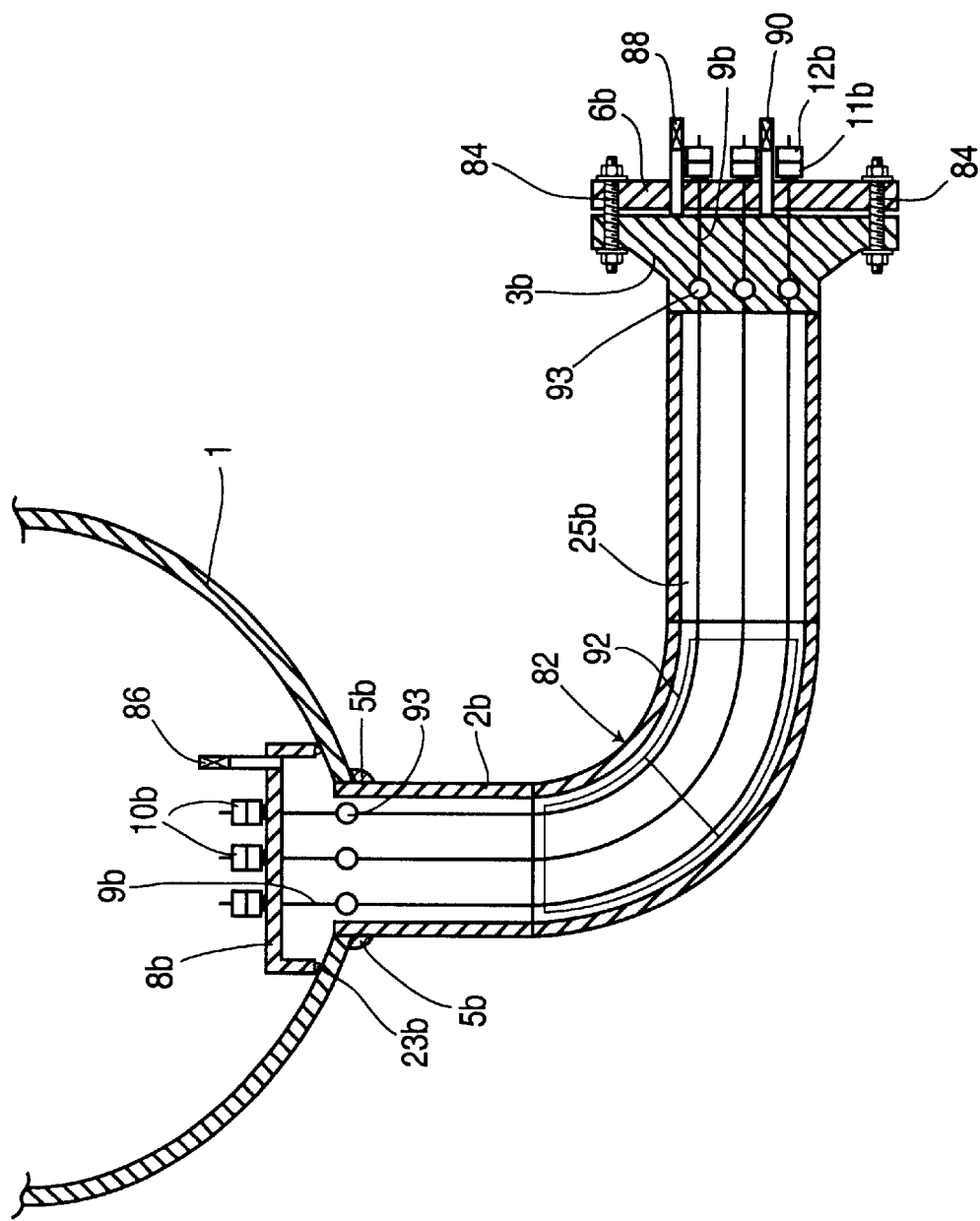

In FIG. 10, a further embodiment of the invention is provided wherein the testing assembly is adapted for use in nozzles incorporating a bend. Elements in this figure that are similar to those in the previous drawings are designated with the letter "b" for convenience. In this case, the nozzle 2b includes a bend 82 between the vessel 1 and the flange 3b. The testing assembly includes a body 8b within the vessel and an external blind 6b connected by at least one tie rod 9b. As before, the body 8b includes a sealing element such as an O-ring 23b for creating a seal between the body 8b and the vessel 1. The external blind 6b is secured to the flange 3b by means of bolts 84 or other such securing means. The body is provided with a port 86 and the blind 6b is provided with ports 88 and 90 for filling and venting the sealed area 25b. In the case of the external blind, one of the ports can also be used for adding a pressure gauge. The tie rods 9b, in this embodiment, are flexible material in order to navigate through the bend 82 and preferably comprise chains. However, the tie rods 9b still perform the same function as before, namely, they are used to tighten the body 8b against the inner wall of the vessel 1 by pulling it towards the external blind 6b. In order to ensure that the force on the body 8b is applied generally perpendicularly, a guide 92 is placed within the bend to the guide the tie rods 9b in the required directions. The guide 92 thus ensures that the body 8b bears against the vessel wall equally on all sides so that an adequate seal is established. As before, the tie rod 9b are connected by means of nuts 10b and 12b and packing boxes 11b. The tie rods 9b, or chains, are also preferably provided with links or grommets 93 for attaching the chains together.

Figure 11:
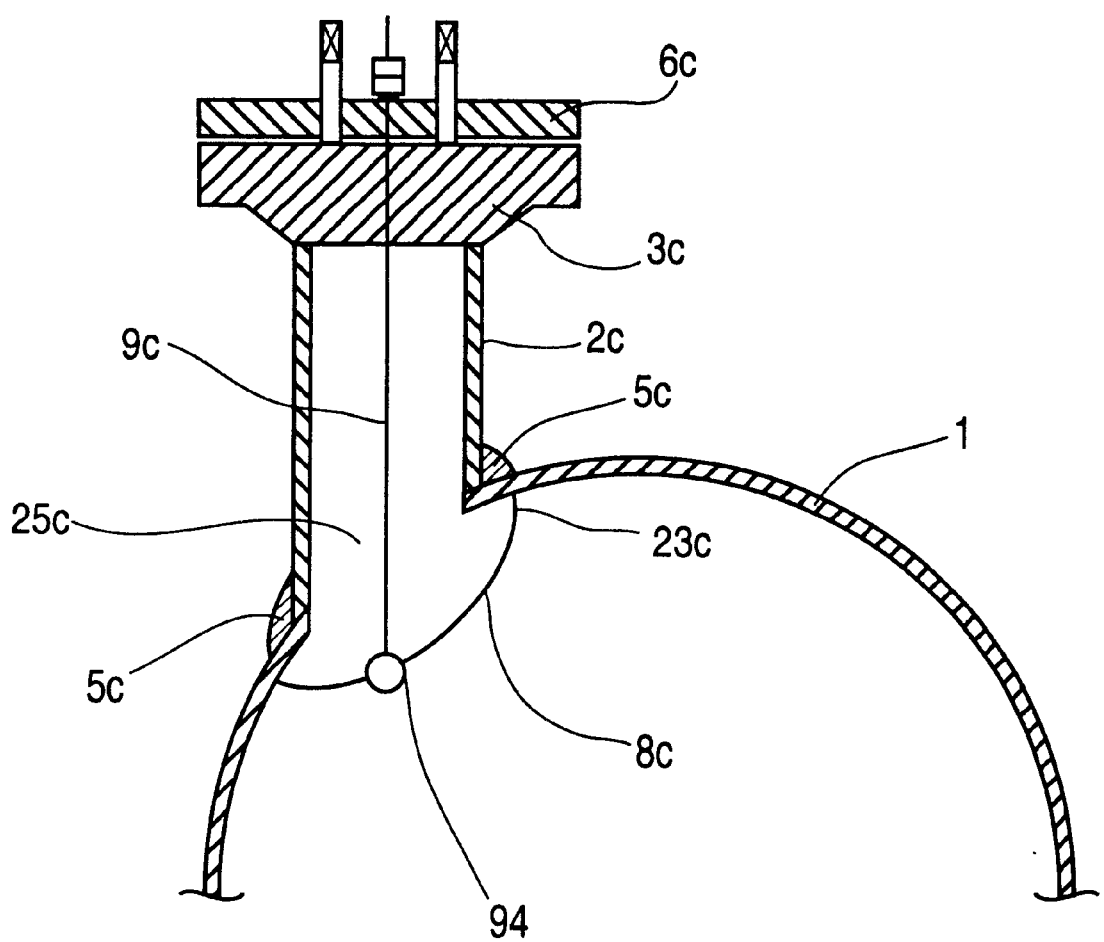

FIG. 11 illustrates a further embodiment of the invention with similar elements designated with the letter "c" for convenience. In this embodiment, the nozzle 2c is offset and attached to a vessel 1 at an angle. Accordingly, to create the required sealed area 25c, the body as shown in FIG. 2 is used and comprises a "universal" body that can be used for different orientations of the nozzle. In this case, the tie rod 9c is capable of being directed in the required direction. This is accomplished by anchoring the tie rod 9c to the body 8c with a swivel joint. The swivel joint preferably comprises a ball 94, such as that of a trailer hitch, to which the tie rod 9c is attached. The means of attachment may be by screwing or welding the rod to the ball or any other means. An opening is provided in the body 8c through which the tie rod 9c is passed, but which is not wide enough for the ball 94 to rotate within. The ball 94 is also provided with a sealing means such as a gasket type material (for example, Teflon™) so that once the tie rod 9c is tightened, the ball 94 forms a leak-proof seal against the opening in the body 8c. In the preferred embodiment, the assembly is provided with one or three tie rods 9c as this arrangement has been found to minimize the "walking", or movement, of the body 8c along the inner wall of the vessel 1.

Figure 12:
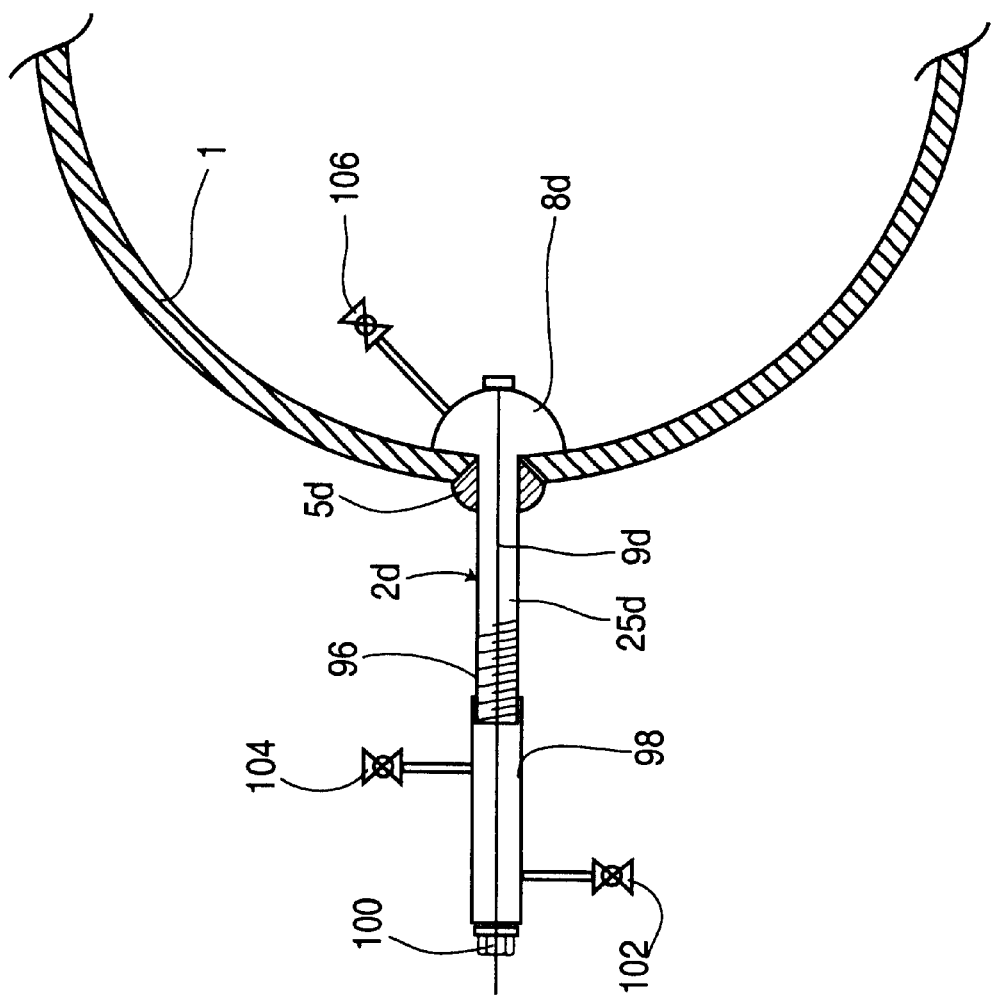

FIG. 12 illustrates yet a further embodiment of the invention with similar elements identified with the letter "d" for convenience. In this embodiment, the nozzle 2d includes a threaded end 96 and does not have a flange. Accordingly, in this embodiment, the external blind is replaced with a sleeve 98 that is screwed onto the threaded portion 96. A tie rod 9d is attached to a body 8d similar to that shown in FIG. 2 and is secured to the sleeve 98 with a nut 100. The sleeve is provided with ports 102 and 104 for filling and venting the sealed area 25d. Further, a port 106 may be provided on the body 8d also for filling or venting the sealed area 25d.

Figure 13:
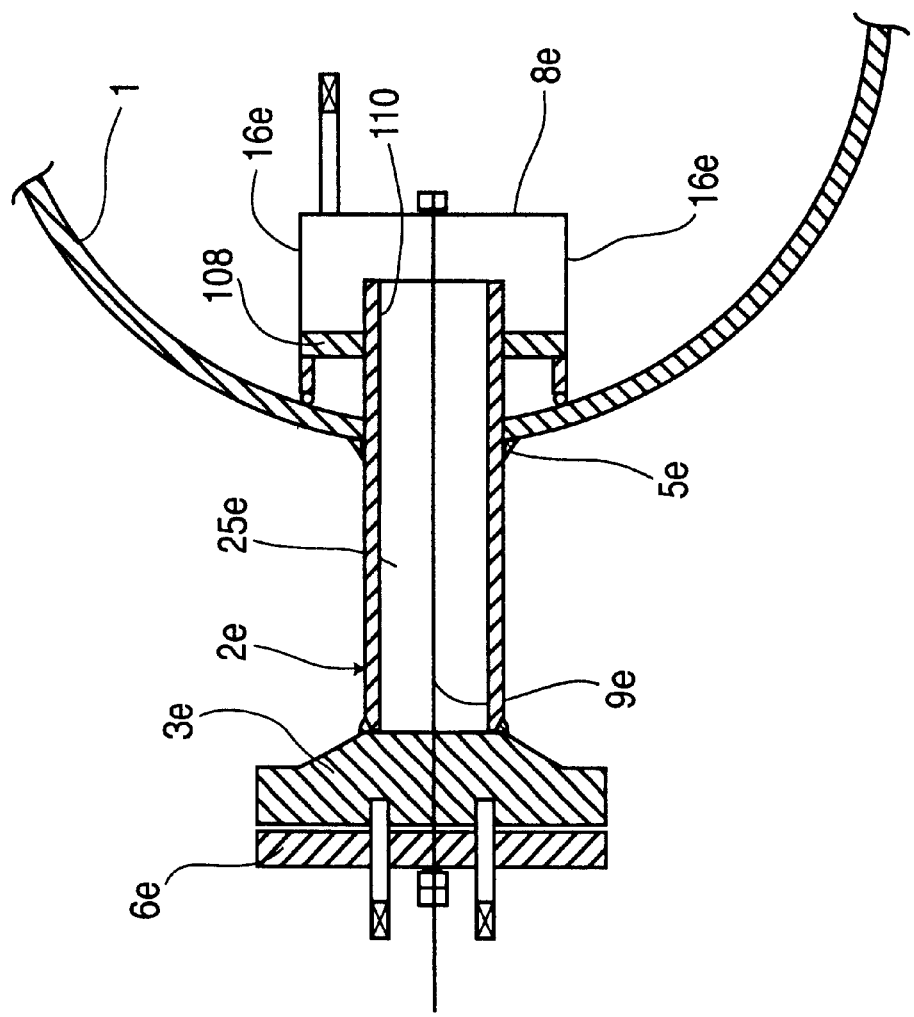

FIG. 13 illustrates another embodiment of the invention with similar elements identified with the letter "e" for convenience. In this instance, the nozzle 2e extends into the vessel 1 by a certain distance to create a protruding portion 110. Accordingly, the body 8e must be designed so that is has elongated side walls 16e that can extend beyond the protrusion 110 of the nozzle 2e in order to contact the inner wall of the vessel 1. A spacer 108 is provided over the protrusion of the nozzle so that the body 8e can be centered over it and also to prevent any movement of the body 8e. the spacer may be an annular structure that is fitted over the protruding portion 110 of the nozzle 2e.

Figure 14:
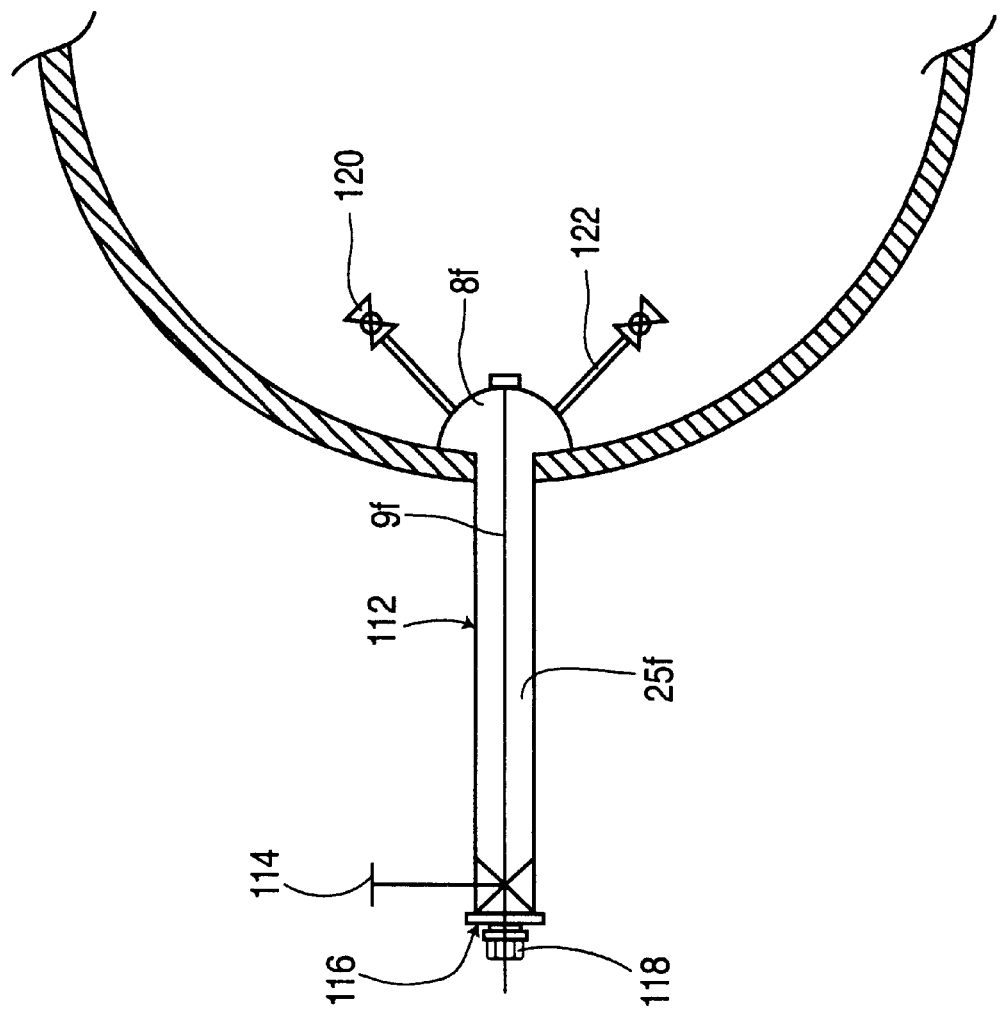

FIG. 14 illustrates an embodiment of the invention, with similar elements identified with "f", wherein the vessel is provided with a pipe 112 with a valve 114, such as a gate or metering valve. Again, the body 8f is similar to that of FIG. 2 and is attached to a tie rod 9f, which is connected, at its other end, to a plate 116 by means of a nut 118. The body 8f is provided with ports 120 and 122 for filling and venting the sealed area 25f.

Figure 15:
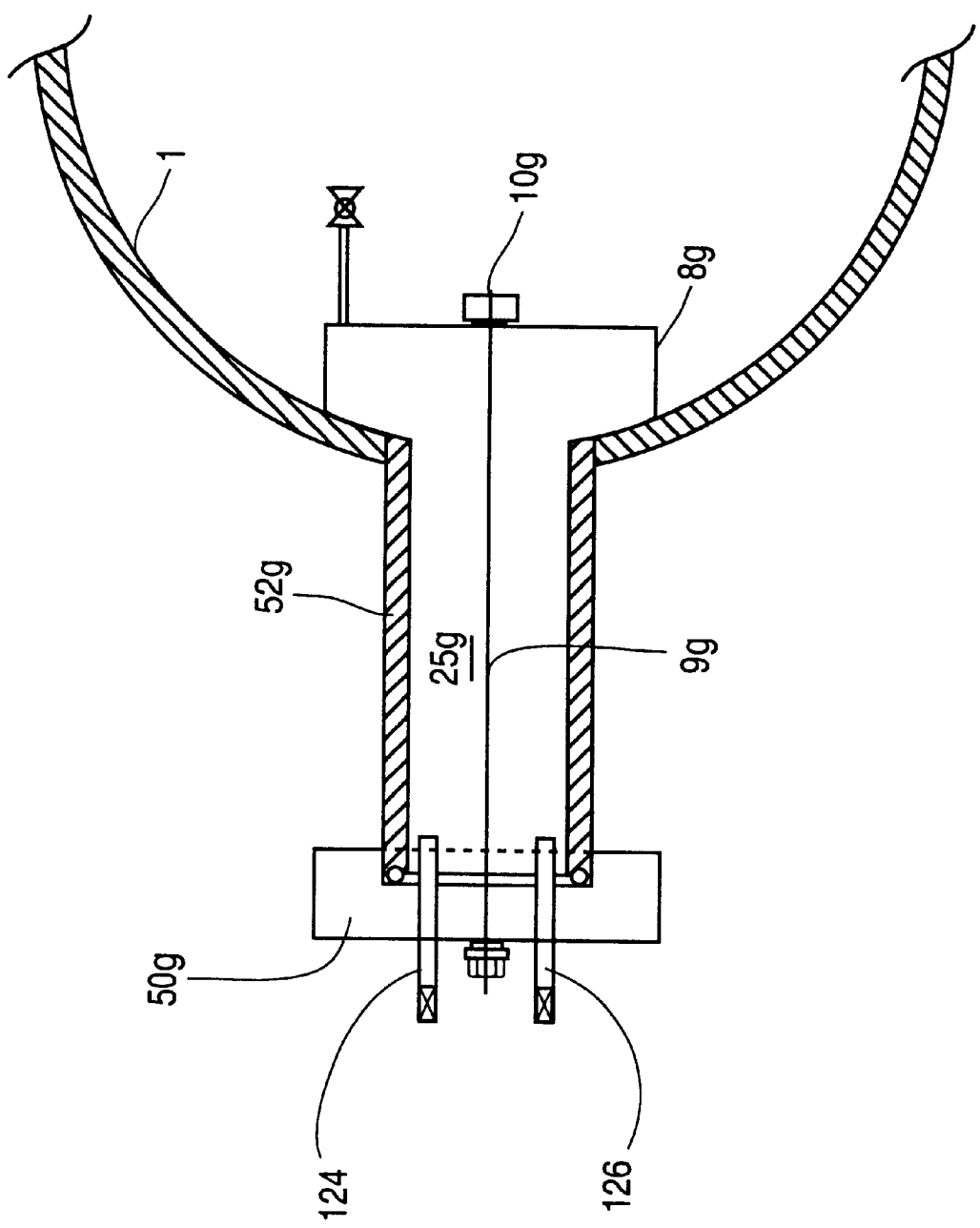

FIG. 15 is a variant of the embodiment shown in FIG. 5, with similar elements identified with "g", wherein the plate 50g is provided with two ports 124 and 126 for filling or venting the sealed area 25g.

In most vessels, the largest opening is generally in the range of 20" to 24" in diameter. However, in order to test welds around such openings, the body of the test assembly must be smaller than the largest opening in order to have such body enter into the vessel. Therefore, a problem occurs when testing such large openings (i.e. openings greater than 20" in diameter) since the body of the test assembly, required for conducting the test, cannot fit into the vessel. For example, for testing vessel openings greater than 20" in diameter, the body of the test assembly is usually 30" in diameter. As such, the body will not be able to enter the vessel in order to conduct the required test. Normally, tests on such "large" openings are carried out by cutting the body into two pieces and welding them together inside the vessel. After the test is complete, the body is once again cut and removed from the vessel. As will be understood, this process involves much more time than regular tests and the life span of the body is reduced. To overcome this problem, the present invention, according to another embodiment, comprises a test assembly generally as described above but including a body consisting of two pieces, or halves, and being capable of being joined together with connectors, such as nuts and bolts and the like.

Figure 16:
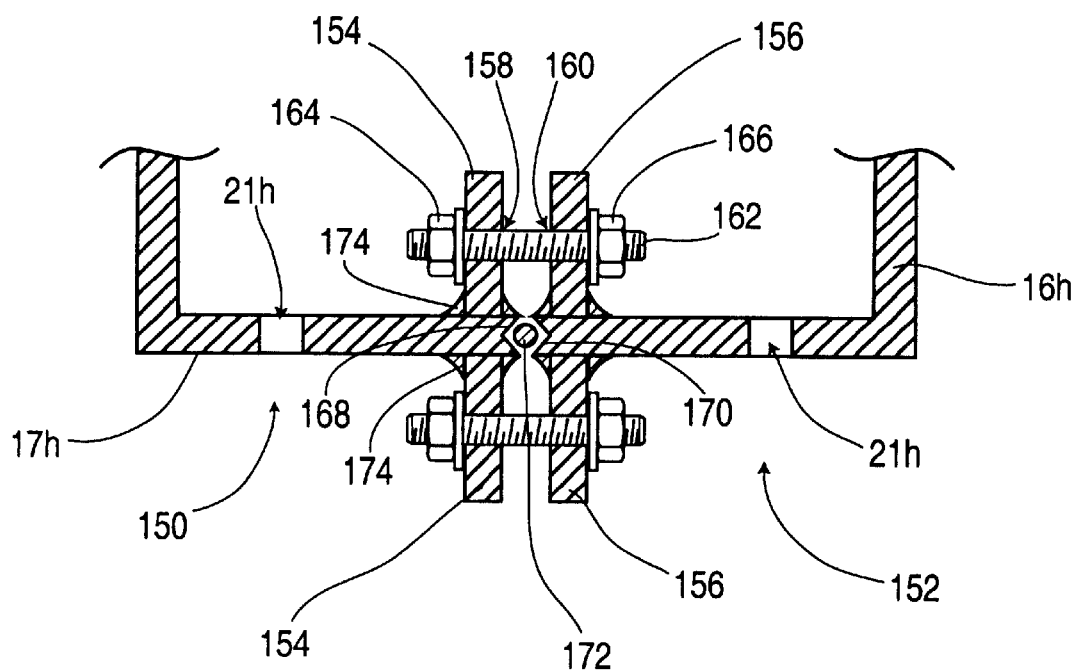
FIG. 16 is a partial cross sectional view of another embodiment of the invention.
Figure 17:
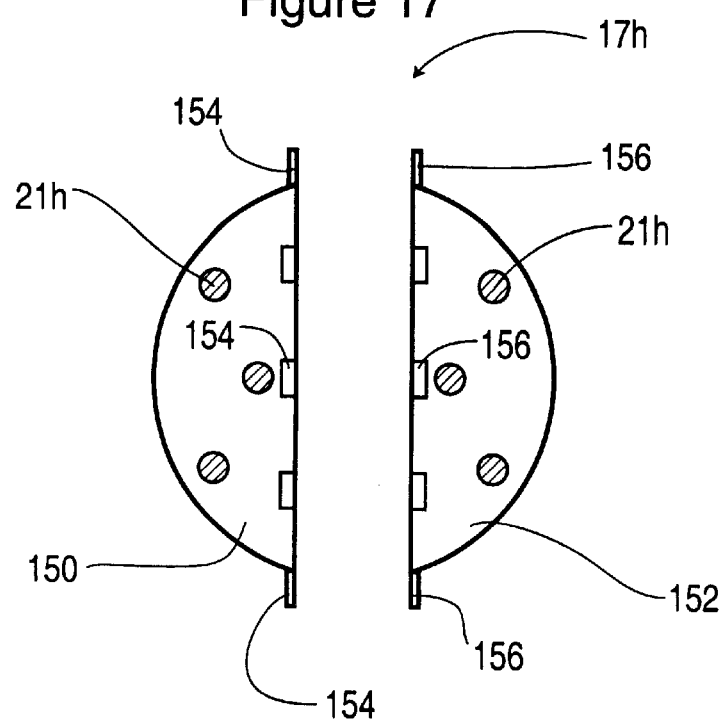
FIG. 17 is an end view of the embodiment of FIG. 16.
Figure 18:
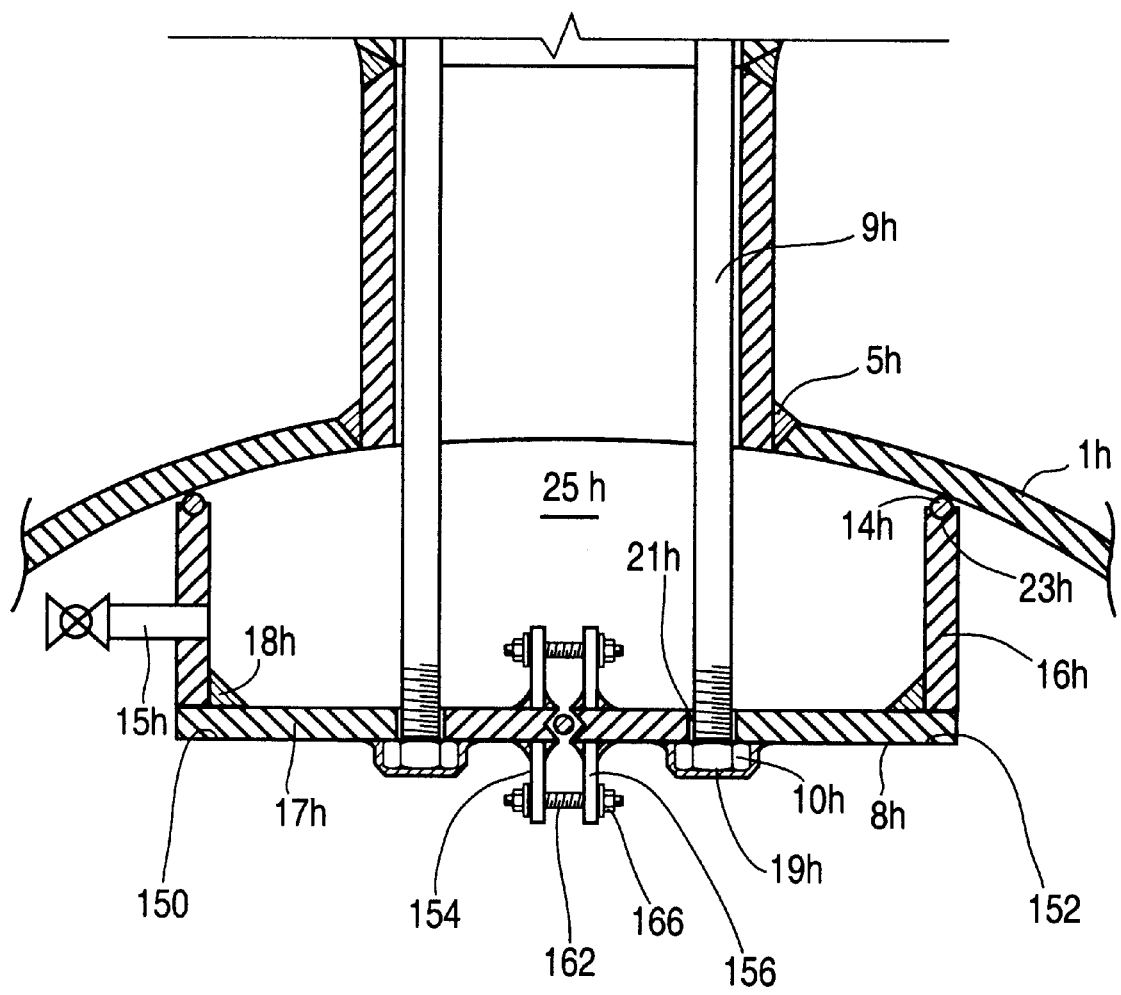
FIG. 18 is a cross sectional view of the embodiment of FIG. 16 when used with the assembly of FIG. 1.

The test assemblies illustrated in FIGS. 16 to 18 may be used for the large vessel openings mentioned above. In FIGS. 16–18, elements that are similar to those mentioned above with reference to other figures are identified with like reference numerals but with the letter "h" added for clarity. For the purpose of the present description, the term "large openings" is considered to comprise openings having a diameter greater than 20". However, it will be understood by persons skilled in the art that the term "large" is discretionary and may comprise any size opening for which a test assembly body is too large to fit inside a vessel.

FIG. 16 illustrates a partial view of a test assembly for use on openings for which a single piece test body cannot be used. As mentioned above, such test assembly is provided with a disc 17h, which includes two separate pieces or sections 150 and 152. The sections 150 and 152 of the disc 17h are provided with a plurality of flanges 154 and 156, respectively, extending generally perpendicularly from the plane of the disc 17h on both sides thereof. Sealing flanges 154 and 156 are provided on pieces 150 and 152 in such manner as to allow the flanges of each piece to oppose each other. The flanges 154 and 156 are also provided with opposing apertures 158 and 160, respectively, through which is passed a bolt 162. Nuts 164 and 166 are provided on opposite ends of bolt 162 whereby tightening of the nuts 164 and 166 forces opposing flanges 154 and 156 to approach each other. In the result, the separate pieces 150 and 152 are brought together thereby to form the disc 17h. In order to achieve a sealing relationship between the pieces 150 and 152 each piece is provided with a notch or groove 168 and 170, respectively, on the adjacent ends thereof. A sealing material such as an "O" ring or gasket, 172, is provided within the space formed by the opposing notches or grooves, 168 and 170. The sealing flanges 154 and 156 may be either formed with each piece 150, 152, or, as shown, may be separate pieces that are attached to each piece 150, 152 by welds 174.

Although the above preferred embodiment describes the use of sealing flanges and associated bolts to connect the pieces, 150 and 152, of the disc 17h, other means of connecting such pieces will be apparent to persons skilled in the art. Further the flanges 154, 156 may be attached to the pieces or sections 150 and 152 in a number of ways as known in the art.

FIG. 17 illustrates an end view of the assembly of FIG. 16. As can be seen, each piece or section, 150 and 152, forming the disc 17h, is provided with a plurality of sealing flanges 154 and 156, respectively. It will be appreciated that the number of flanges required will be dependent on the diameter of the disc 17h being formed. Further, it will be apparent to persons skilled in the art that the number of flanges 154, 156 may be reduced by providing one or more long flanges on each piece 150, 152, each of such flanges being connected to an opposing flange by one or more bolts.

FIG. 18 illustrates the assembly of FIG. 1 wherein the opening to be tested has a diameter greater than 24". In such case, the disc 17 is formed with the embodiment shown in FIG. 16. Therefore, the disc 17h is formed by the opposing pieces or halves 154 and 156.

Figure 19:
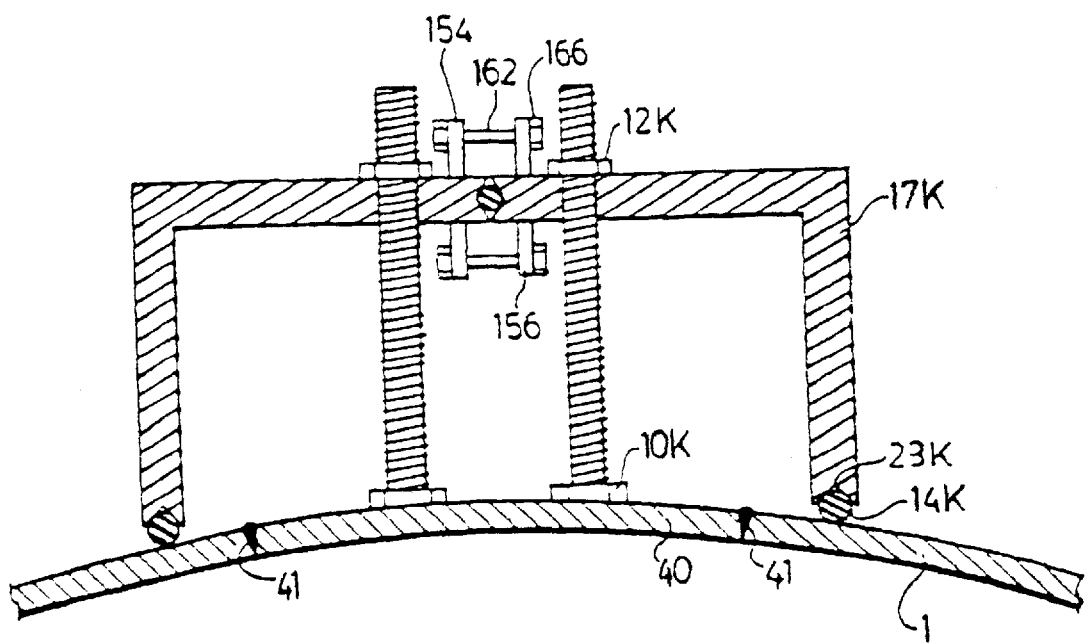
FIG. 19 is a cross sectional view of the embodiment of FIG. 16 for use on a patch in the wall of the vessel.

FIG. 19 illustrates the two part test assembly for testing the welds of a patch on a vessel wall.

Although the invention has been described with reference to certain specific embodiments, various modifications thereof will be apparent to those skilled in the art without departing from the spirit and scope of the invention as outlined in the claims appended hereto.

What is claimed is:

1. A weld testing assembly for hydrostatic pressure testing of welds between a patch connecting two components, said weld testing assembly comprising:

a body securable against at least one surface of at least one of said components so as to define a sealed space adjacent to the weld to be tested; and at least one port for receiving a pressurized test fluid into said sealed space;

said body being provided with one or more threaded tie rods and one or more nuts adapted to be threaded on said tie rods;

said at least one tie rod is secured to said patch and tightening of said nut forces said body towards said patch, said body extending beyond said patch such that said sealed space includes said weld.

2. A method for testing a weld between a first component and a patch on the first component, comprising the steps of:

providing a sealing assembly comprising a body adapted to be forced into engagement with at least one surface of said first component, said body extending beyond said patch;

providing at least one threaded tie rod secured to said patch;

securing said sealing assembly against said at least one surface so as to define a sealed space adjacent to, and including, the weld to be tested, said sealing assembly being secured against said at least on surface by tightening a nut on each of said at least one threaded tie rod such that tightening of said nut pulls said body towards said patch;

injecting a pressurized test fluid into said sealed space; and monitoring said sealed space for indicia of a leak of said test fluid from said sealed space.

3. The weld testing assembly of claim 1, wherein said body is comprised of two or more sections, each of said sections including a means for joining said sections together to form said body.

4. A weld testing assembly for hydrostatic pressure testing of welds between two components, said weld testing assembly comprising:

a body securable against at least one surface of at least one of said components so as to define a sealed space adjacent to the weld to be tested; and at least one port for receiving a pressurized test fluid into said sealed space;

said body being provided with one or more threaded tie rods and one or more nuts adapted to be threaded on said tie rods;

wherein said body is comprised of two or more sections, each of said sections including a means for joining said sections together to form said body.

5. A weld testing assembly as recited in claim 4, where said body is securable against said at least one surface by tightening a nut on each of at least one threaded tie rod, where said tie rod is secured relative to said components such that tightening of said nut acts to force said body towards said component.

6. A weld testing assembly as recited in claim 5, where said assembly is adapted for testing a weld between a nozzle and a pressure vessel, said nozzle extending from said pressure vessel and terminating in a flange, said assembly having a blind securable onto said flange, said body being positioned within said pressure vessel, and said at least one tie rod being positioned between said blind and said body to pull said blind and said body towards each other, thereby sealing said body against said pressure vessel to define said sealed space.

* * * * *